United States Patent [19]

Teubner

[11] 4,289,402
[45] Sep. 15, 1981

[54] SPARK CHAMBER FOR A VACUUM EMISSION SPECTROMETER

[75] Inventor: Ehrhardt Teubner, Ingolstadt, Fed. Rep. of Germany

[73] Assignee: Schubert & Salzer, Ingolstadt, Fed. Rep. of Germany

[21] Appl. No.: 63,200

[22] Filed: Aug. 3, 1979

[51] Int. Cl.³ .............................................. G01J 3/10
[52] U.S. Cl. ..................................... 356/313; 356/244
[58] Field of Search ................................ 356/313, 244

[56] References Cited

U.S. PATENT DOCUMENTS 3,711,201 1/1973 Sturlese et al. ..................... 356/313

Primary Examiner—Vincent P. McGraw
Attorney, Agent, or Firm—Bailey, Dority & Flint

[57] ABSTRACT

A spark chamber for a vacuum emission spectrometer with a housing, which accommodates an anode, as well as a sample table plate carried by the housing, on which the piece of material being inspected and making up the cathode is placed and which carries a spark centering plate. The sample plate (5) includes a molded laminate material, whose sides (501) facing the anode (23) has a polished surface.

7 Claims, 2 Drawing Figures

SPARK CHAMBER FOR A VACUUM EMISSION SPECTROMETER

BACKGROUND OF THE INVENTION

The present invention relates to a spark chamber for a vacuum emission spectrometer with a housing, which accomodates an anode, as well as a sample table plate carried by the housing, on which a piece of material being inspected and making up the cathode is placed and which carries a spark centering plate.

In a vacuum emission spectrometer of this type the light emitted from a sample will be dispersed in its spectral colors and then measured. For this purpose it will be necessary to increase the energy level of the electrons orbiting around the nucleus in fixed orbits by temporarily supplying energy. This condition is instable, so that the electrons will fall back to their old level. These electron jumps will release energy, which will be radiated in the form of light rays.

Energy must be supplied in order to temporarily bring the electrons in an orbit of higher energy level. This is accomplished with sparks, which are produced between two electrodes. These sparks will tear out small particles from the piece of material being inspected, which then reach into the spark chamber. Consequently in the practice both the housing as well as the sample table plate, on which the sample being inspected is placed, are designed as ceramic parts. Because of permanent loads the service life of in particular the very expensive ceramic sample table plate is extremely short, so that this device cannot be operated very economically.

Consequently the task of the present invention shall be to provide a spark chamber for a vacuum emission spectrometer, of which the parts subject to wear are considerably more resistant to wear and therefore have a considerably longer service life than those of know devices, so that they can be operated more economically than these.

SUMMARY OF THE INVENTION

This task is solved according to the invention, in that the sample table plate is made of moulded laminated material or a heat stabilizing plastic, whose side facing the anode has a polished surface. The moulded laminated material or heat stabilizing plastic is exceptionally lowpriced in comparison to ceramics. But in addition to this it has been proven, that when the moulded laminated material or heat stabilizing plastic sample table plate has a polished surface side facing the anode, the particles of material flying around inside of the spark chamber will rebound off of the sample table plate, without damaging it or settling on it. In this manner the sample table plate according to the present invention has a service life more than five times longer than that of known sample table plates made of ceramics. It has also been proven in addition to this, that because of this, the sparks rebound from the smooth surface of the sample table plate according to the present invention immediately, without being heated beyond a tolerable degree. Astonishedly not only the service life of the sample table plate is longer than that of previously known sample table plates, but also the spark centering plate carried by the sample table plate vaporizes much slower. This spark centering plate is particularly subjected to energy and heat originating from the electrodes, so that for this part even more valuable and therefore more expensive material could be applied, which then would have considerable influence on the economical operation of the vacuum emission spectrometer.

In a further version of the present invention the housing as also the sample table plate would be made of a moulded laminated material or heat stabilizing plastic and would also have a polished surface on its inside. With the same function an extremely resistant spark chamber would be provided in this manner. With the previously known housings for the spark chamber the anode could only be held in position by pasting it on the housing. By designing the housing made of moulded laminated material or a heat stabilizing plastic it will be possible to carry the anode on a holding plate bolted to the housing.

Resin bonded paper will be preferred for use as the moulded laminated material.

In order to even further improve the already long service life of the object of the present invention, the installation of a heat dissipator will be preferred between the piece of material and cathode, which in accordance with the especially simple design of the object of the present invention is designed as an exchangeable copper block.

In comparison with previously known spark chambers for a vacuum emission spectrometer the object of the present invention is consequently considerably more resistant and wearproof and therefore has a much longer service life while performing the same functions, so that the spark chamber according to the present invention is more economical than the previously known spark chambers.

Further details of the object in the present invention will be more closely described in the text below on the basis of drawings, which show:

DESCRIPTION OF A PREFERRED EMBODIMENT

Figure 1:
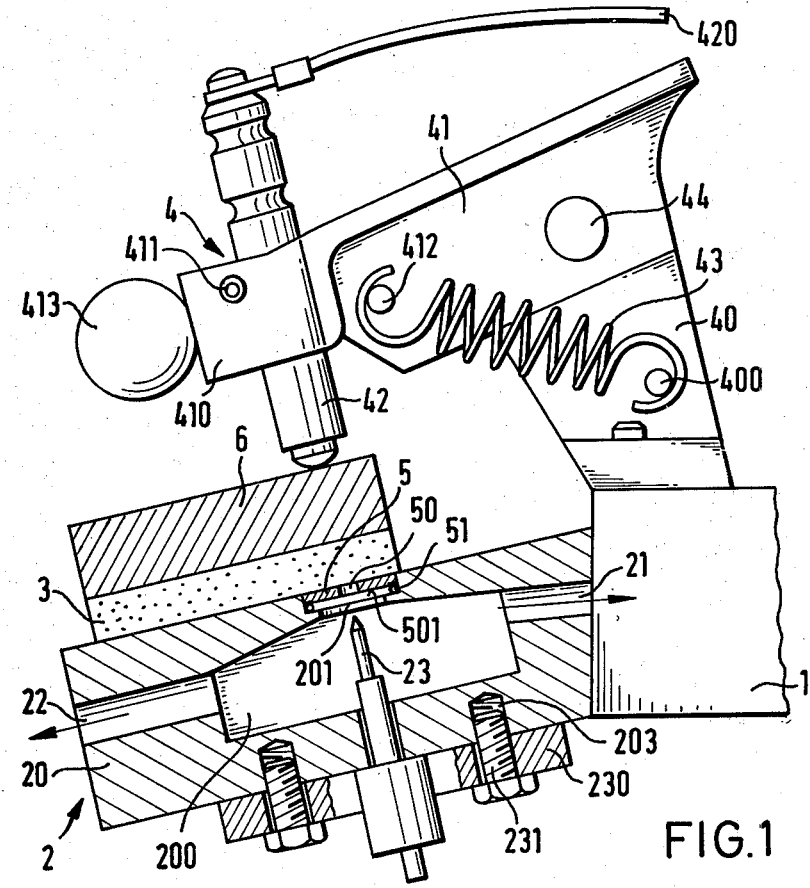
FIG. 1 is a section view of the vacuum emission spectrometer spark chamber designed according to the present invention.

As shown in FIG. 1, spark chamber 2 is mounted on framework 1 of the vacuum emission spectrometer. The framework 1 of the vacuum emission spectrometer takes the normal grating and photodiodes, which disperse the emitted light into its individual light bands and determine the intensity of the different light bands. The values received in this manner identify the composition of the inspected piece of material 3.

The spark chamber 2, on whose top surface the piece of material 3 being inspected is placed, posseses a housing 20 with an inside chamber 200, which is connected with the inside of framework 1 by way of one passage 21 and a gas supply line (not shown) provided at this location and with a gas outlet line (not shown) by way of a second passage 22. The light emitted by the inspected piece of material 3 passes through the first passage 21 to the grating and photodiodes to determine the material composition on the basis of availability and intensity of different bands from the emitted light. In addition, this passage 21 is used to supply noble gas, normally argon, so that sparks can be produced in this noble gas atmosphere. The second passage 22 is employed to extract the air and noble gas from the housing 20. Consequently the inside chamber 200 will be flushed with noble gas for the time of spark production.

From the side facing away from the piece of material 3 being inspected, i.e. from the bottom of housing 20, an electrode serving as an anode 23 protrudes into the inside chamber 200 of housing 20, which is connected with a source of power not shown in the drawing. The anode 23 is carried by a holding plate 230, which is mounted on housing 20.

Figure 2:
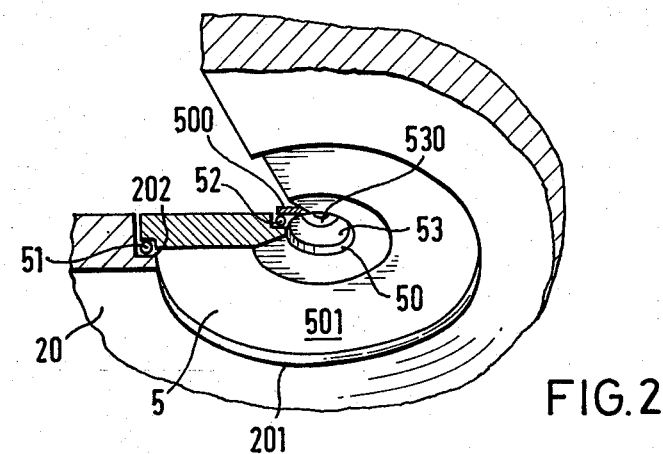
FIG. 2 is a perspective, partially sectioned, view of the sample table plate according to the present invention.

The top surface of housing 20 has an opening 201 increasing in size by steps toward the outside, in which a sample table plate 5 is located (FIG. 2). A seal 51 is inserted between the face surface 202 of the shoulder of opening 201 and the sample table plate 5. The sample table plate 5 has for its part an opening 50, which also increases in size by steps toward the outside. In this manner a ring-shaped face surface 500 is produced, on which the spark centering plate 53 is positioned together with a further seal 52 inbetween. The spark centering plate 53 has for its parts a centrical opening 530, through which the anode 23 can take affect on the piece of material 3 being inspected.

In accordance with the present invention the sample table plate 5, which allows access to the inside chamber 200 of housing 20, is made of a moulded laminated material or heat stabilizing plastic and has a polished surface on its side 501 facing the anode 23. A heat stabilizing plastic must be understood as a plastic, which is extremely heat-proof due to the addition of a heat stabilizer.

The piece of material 3 being inspected is held on the top surface of spark chamber 2 by a mounting device 4 (FIG. 1). The mounting device 4 consists of a holder 40 mounted on the framework 1, on which a swinging arm 41 is attached by way of a swinging shaft 44. The free end 410 of the swinging arm 41 holds the electrode serving as a cathode 42, which is mounted with a holding screw in the swinging arm 41. The cathode 42 is connected with a source of power not shown in the drawing by a wire 420. One each spring bolt 400 or 412 is mounted on the holder 40 as well as swinging arm 41, on which a spring 43 is attached. The spring 43 provides an elastic holding of the piece of material 3 being inspected on the top surface of spark chamber 2.

For operation the swinging arm 41 is fitted with a grip 413.

The device, whose design was described above, functions as follows:

With grip 413 the swinging arm 41 is lifted temporarily, so that the piece of material 3 being inspected can be placed on the top surface of housing 20. For this purpose the piece of material 3 was previously given a smooth top and a smooth bottom surface. By lowering the swinging arm 41 the force of spring 43 will clamp the piece of material 3 between the cathode 42 and the top surface of housing 20. This will seal the housing 20, since the opening 530 in the spark centering plate 53 will be covered. Through passages 21 and 22 the housing 20 will be flushed with a noble gas and the air will be extracted from spark chamber 2. Now anode 23 and cathode 42 receive electric power. This will produce sparks between the anode and the clamped piece of material 3, which cause the electrons of atoms of the different elements contained in the piece of material 3 to temporarily go to outer orbits. When returning to the normal inner orbits they will emit a light specific for each element, which passes through passage 21 into the framework 1 of the vacuum emission spectrometer for analysis, where the band and intensity of the emitted light rays are determined.

With the sparks taking effect on the piece of material 3, the energy and heat will be concentrated on the surface of the piece of material 3 inside of the opening 530 by way of the spark centering plate serving as a lens.

In spite of this it cannot be avoided that sparks also reach the sample table plate 5. However, because of its polished surface on the side 501 facing the anode 23 it lets them rebound with practically no effect. There is no heating beyond a tolerable degree, since the piece of material 3 dissipates the heat immediately. The smooth surface of the side of the sample table plate 5 facing the anode 23 also impairs the settling of material particles, so that there can be more time between cleaning ineteryals. Cleaning is also easier because of the smooth surface.

After conclusion of spark production lasting only several seconds the supply of electric power to the electrodes (anode 23 and cathode 42) will be interrupted. After lifting the swinging arm 41 the piece of material 3 can be removed and when applicable replaced by a new piece of material 3 to be inspected.

Where in the past ceramics were used for the sample table plate 5 and had to be manufactured by pressing, manufacturing by cutting is now possible. It has been proven that moulded laminated materials as well as heat stabilizing plastics are suitable for use as material of the sample table plate 5. By example resin bonded paper is employed in accordance with a preferred version. A sample table plate 5 according to the present invention is considerably more advantageous because of the more simple processing of these materials as compared with the previously common ceramics. In addition, the service life of the sample table plate 5 is astonishedly many times longer than that of the previous sample table plate 5.

The service life can be extended even further in that a heat dissipator be installed between the piece of material 3 being inspected and the cathode 42. This heat dissipator 6 consists of a material with good heat conductive properties, which dissipates the heat produced in the piece of material 3, so that the sample table plate 5 will be heated less than without said heat dissipator. Preferably the heat dissipator 6 would consist of a copper block, which after inspection of one or more samples, if it has become extremely hot, is not inserted with a new piece of material 3, but exchanged against a different copper block.

Astonishedly not only the service life of the sample table plate 5 designed in accordance with the present invention is extended, but even the unchanged and up to now common spark centering plate 53 has a longer service life. While when using ceramics for the sample table plate 5 the boron nitride spark centering plate 53 became continuously thinner within a short time because of evaporation, the service life is extended many times for this type of spark centering plate 53 used in conjunction with a sample table plate 5 designed according to the present invention.

It has been proven that the advantages accomplished for the sample table plate 5 designed according to the present invention could also be applicable to the housing 20, if it were also made of a moulded laminated material or heat stabilizing plastic, as the sample table plate 5, and had a polished surface in its inside adjacent to the inside chamber 200. In addition, this type of housing 20 permits, since it can be produced by cutting in a machine, the provision of tapped bores 203, in which mounting bolts 231 for the holding plate 230 of the anode 23 can be screwed in. There can now be a safe bolted connection, instead of the previously necessary, not very permanent and consequently unsafe pasting of the anode 23 on the housing 20.

Therefore with the same application for spectral analysis the object according to the present invention can be manufactured more economically and also has a considerably longer service life. In addition, it is less inclined to contamination through the settling of particles of material on the inside of the spark chamber as in the previously known spark chambers and is also easier to clean at intervals of time more widely spread, than was previously possible.

I claim:

1. A spark chamber for a vacuum emission spectrometer with a housing, which accommodates an anode, as well as a sample table plate carried by the housing, on which the piece of material being inspected and making up the cathode is placed and which carries a spark centering plate, distinguished by the fact that the sample table plate (5) includes a moulded laminated material, whose side (501) facing the anode (23) has a polished surface.

2. A spark chamber for a vacuum emission spectrometer with a housing, which accommodates an anode, as well as a sample table plate carried by the housing, on which the piece of material being inspected and making up the cathode is placed and which carries a spark centering plate, distinguished by the fact that the sample table plate (5) includes a heat stabilizing plastic, whose side (501) facing the anode (23) has a polished surface.

3. A spark chamber according to claim 1 or 2, distinguished by the fact that the housing (20) as well as the sample table plate (5) are made of moulded laminated material or heat stabilizing plastic and have a polished surface on their inside.

4. A spark chamber according to claim 3, distinguished by the fact that the anode is carried by a holding plate (230) bolted (parts 203 and 231) to the housing (20).

5. A spark chamber according to claim 1 further comprising:
   said molded laminated material being a resin bonded paper.

6. A spark chamber according to claim 1 further comprising:
   a heat dissipator being located between said piece of material and said cathod.

7. A spark chamber according to claim 6 further comprising:
   said heat dissipator being an exchangeable copper block.

* * * * *